(12) United States Patent
Ahmed et al.

(10) Patent No.: US 7,795,237 B2
(45) Date of Patent: Sep. 14, 2010

(54) PHARMACEUTICAL COMPOSITION AND PROCESS

(76) Inventors: Hashim A. Ahmed, 14 Winding Way, Princeton, NJ (US) 07012; Thomas Vernon Alfredson, 4135 Dake Ave., Palo Alto, CA (US) 94306; Kondamraj Birudaraj, 507 Crestview Ave., #118, Belmont, CA (US) 94002; Michael Thomas Brandl, 2460 Oregon Ave., Redwood City, CA (US) 94061; Wantanee Phuapradit, 4 Effingham-Low Ct., Montville, NJ (US) 07045; Navnit Hargovindas Shah, 203 Beverly Hill Rd., Clifton, NJ (US) 07012; Dimitrios Stefanidis, 278 Monroe Dr., No 14, Mountain View, CA (US) 94040

( * ) Notice: Subject to any disclaimer, the term of this patent is extended or adjusted under 35 U.S.C. 154(b) by 922 days.

(21) Appl. No.: 11/637,999

(22) Filed: Dec. 13, 2006

(65) Prior Publication Data

US 2007/0202175 A1    Aug. 30, 2007

Related U.S. Application Data

(60) Provisional application No. 60/750,146, filed on Dec. 14, 2005, provisional application No. 60/830,594, filed on Jul. 12, 2006.

(51) Int. Cl.
- *A01N 43/04* (2006.01)
- *A61K 9/14* (2006.01)
- *A61K 9/20* (2006.01)
- *A61K 9/50* (2006.01)
- *A61K 31/70* (2006.01)

(52) U.S. Cl. ............... 514/49; 424/464; 424/489; 424/499

(58) Field of Classification Search .............. None
See application file for complete search history.

(56) References Cited

U.S. PATENT DOCUMENTS

| | | | |
|---|---|---|---|
| 6,488,963 | B1 | 12/2002 | McGinity et al. |
| 6,846,810 | B2 * | 1/2005 | Martin et al. ............ 514/49 |
| 2004/0253314 | A1 | 12/2004 | Petereit et al. |
| 2005/0044529 | A1 | 2/2005 | Simons et al. |
| 2005/0048112 | A1 | 3/2005 | Breitenbach et al. |

FOREIGN PATENT DOCUMENTS

| WO | WO 02/089835 A1 | 11/2002 |
|---|---|---|
| WO | WO 2004/046159 A1 | 6/2004 |

OTHER PUBLICATIONS

Alvarez-Nunez, F.A. et. al. Formulation of a Poorly Soluble Drug Using a hot Melt Extrusion, *Amer. Pharm. Rev.* (2004) 7(4), pp. 88-92.
Breitenbach, J. "Melt Extrusion: from process to drug delivery technology," *Euro. J. Pharm. And Biopharm.* (2002) vol. 54, pp. 107-117.
Breitenbach, J "Melt Extruded Molecular Dispersions," Drugs Pharm. Sci. (2003) vol. 133, pp. 245-260.
Chiou, W.L. et. al. "Pharmaceutical Applications of Solid Dispersion Systems," *J. Pharm. Sci.* (1971) 60(9), pp. 1281-1301.
Forster, A. et. al. "Selection of Suitable Drug and Excipient Candidates to Prepare Glass Solutions by Hot Melt Extrusion for Immediate Release Oral Formulations," *Pharm. Technol. Eur.* Oct. 2002, pp. 27-37.
Leuner, C., et. al., "Improving Drug Solubility for Oral Delivery using a Solid Dispersions," *Euro. J. Pharm. And Biopharm.* (2000) vol. 50, pp. 47-60.
Serjuddin, A. T. M. Solid Dispersion of Poorly Water-Soluble Drugs: Early Promises, Subsequent Problems, and Recent Breakthroughs, *J. Pharm. Sci.* (1999) 88 (10), pp. 1058-1066.

* cited by examiner

*Primary Examiner*—Traviss C McIntosh, III
(74) *Attorney, Agent, or Firm*—Brian L. Buckwalter

(57) ABSTRACT

The present invention relates to a pharmaceutical composition comprising a solid suspension prepared by hot melt extrusion of isobutyric acid (2R,3S,4R,5R)-5-(4-amino-2-oxo-2H-pyrimidin-1-yl)-2-azido-3,4-bis-iso-butyryloxy-tetrahydro-furan-2-ylmethyl ester; hydrochloride salt (I) and a polyethylene glycol (PEG)/polypropylene glycol (PPG) block copolymer.

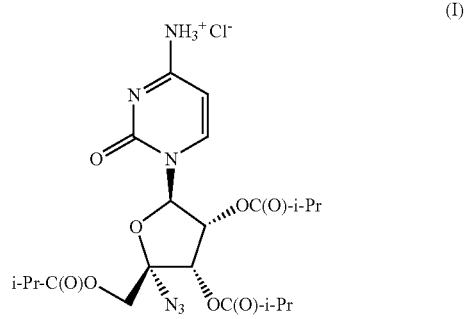

(I)

14 Claims, No Drawings

PHARMACEUTICAL COMPOSITION AND PROCESS

CROSS REFERENCE TO RELATED APPLICATIONS

This application claims the benefit of priority to U.S. Ser. No. 60/750,146 filed Dec. 14, 2005 and U.S. Ser. No. 60/830,594 filed Jul. 12, 2006, the contents of both are hereby incorporated in their entirety by reference.

FIELD OF THE INVENTION

The present invention relates to a novel formulation having as an active ingredient 4'-azidocytidine-2',3',5'-tri-iso-butyrate hydrochloride (I) and a process for preparing the formulation. The composition is useful in the therapy of hepatitis C virus (HCV).

BACKGROUND OF THE INVENTION

Nucleoside derivatives often are potent anti-viral (e.g., HIV, HCV, Herpes simplex, CMV) and anti-cancer chemotherapeutic agents. Unfortunately their utility is often limited by two factors. Firstly, poor pharmacokinetic properties frequently limit the absorption of the nucleoside from the gut and the intracellular concentration of the nucleoside derivatives and, secondly, suboptimal physical properties restrict formulation options which could be employed to enhance delivery of the active ingredient.

Prodrugs (P. Ettmayer et al., *J. Med Chem.* 2004 47(10): 2393-2404; K. Beaumont et al., *Curr. Drug Metab.* 2003 4:461-485; H. Bundgaard, *Design of Prodrugs: Bioreversible derivatives for various functional groups and chemical entities* in *Design of Prodrugs*, H. Bundgaard (ed) Elsevier Science Publishers, Amersterdam 1985; G. M. Pauletti et al. *Adv. Drug Deliv. Rev.* 1997 27:235-256; R. J. Jones and N. Bischofberger, *Antiviral Res.* 1995 27; 1-15 and C. R. Wagner et al., *Med. Res. Rev.* 2000 20:417-45) afford one technique to improve absorption of the drug. Typical examples of prodrugs include compounds that have chemically labile groups linked to a functional moiety of the active compound. Alkylation, acylation or other lipophilic modification of the hydroxy group(s) on the sugar moiety have been utilized in the design of pronucleotides. These pronucleotides can be hydrolyzed or dealkylated in vivo, either enzymatically or chemically mediated, to generate the active compound.

Unfortunately many otherwise useful prodrugs exhibit limited aqueous solubility which present a significant formulation challenge. Traditional solutions to poor aqueous solubility include micronization to lower particle size and, when feasible, conversion of a neutral compound into a more water soluble salt.

Solid dispersions afford one approach to formulation of compounds with poor aqueous solubility. The utility of solid dispersion systems for pharmaceutical formulation applications has been reviewed (W. L. Chiou and S. Riegelman, *J. Pharm. Sci.* 1971 60(9):1281-1302; C. Leuner and J. Dressman, *Eur. J. Pharm. Biopharm.* 2000 50:47-60; A. T. M. Serajuddin, *J. Pharm. Sci.* 1999 88(10):1058-1066, A. Forster et al. *Pharm. Technol. Eur.* 2002 14(10):27; J. Breitenbach *Eur. J. Pharm. and Biopharm.* 2002:54:107-117; J. Breitenbach and M. Mägerlein *Drugs and the Pharmaceutical Sciences* 2003 133:245-260 and K. A. Coppens et al., *Pharm. Technol.* 2006 30(1):62-70). Solid dispersion systems include eutectic mixtures, solid solutions and suspensions, glass suspensions and solutions, amorphous precipitates in crystalline carriers. Solid dispersions are a convenient and effective technique to formulate poorly soluble active ingredients. Disintegration and dispersal of the solid solution or suspensions affords fine colloidal particles of the active ingredient which aid absorption of the active ingredient (AI) in the gastrointestinal (GI) tract.

Solid dispersions can be prepared by hot melt extrusion of a molten mixture of AI and carrier or by rapid evaporation of a solvent from a solution of the AI and a carrier. Various solid carriers have been incorporated into solid dispersions including polyethylene glycol (PEG), polyethyleneoxide (PEO), polyvinylpyrrolidine (PVP), polyvinylalcohol (PVA), hydroxypropyl methyl cellulose (HMPC), hydroxypropyl cellulose (HPC), carboxymethylethylcellulose (CMEC), hydroxypropylmethyl cellulose phthalate (HPMCP), polyacrylates, polymethylacrylates, urea and sugars (e.g., mannitol) (Leuner, supra). While numerous options clearly exist, identifying a carrier molecule with optimal properties for an individual active ingredient remains a significant task.

Among the first and most intensively studied solid dispersion formulations is griseofulvin and PEG (W. L. Chiou and S. Riegelman, supra). PEGs are available over a very broad range of molecular weights and PEG's with molecular weights of approximately 2,000 to 6,000 have optimal physical properties for preparing solid dispersions with griseofulvin. Griseofulvin has limited aqueous solubility and is notoriously poorly absorbed by the oral route. Solid dispersions of griseofulvin and PEG are marketed as Gris-PEG®. PEGs are not good surfactants and the incorporation of emulsifiers, e.g., polysorbate 80, polyethylenedodecyl ether (Brij® 35) or sodium dodecyl sulfate, into the solid dispersion enhanced the dissolution process. An increase in release rate by formulation as a solid dispersion in PEG4000 has been observed for other drugs including oxazepam (J. M. Gines et al., *Int. J. Pharm.* 1996 143:247-253), piroxicam (M. Fernandez et al., *Int. J. Pharm.* 1993 98:29-35), zoldipem (G. Trapani et al., *Int. J. Pharm.* 1999 184:121-130), ketoprofen (M. V. Margarit and I. C. Rodriguez, *Int. J. Pharm.* 1994 108:101-107), oxepam (R. Jachowicz et al., *Int. J. Pharm.* 1993 99:321-325), nifedipine (H. Suzuki et al., *Chem. Pharm. Bull.* 1997 45:1688-1693), phenytoin (R. Jachowicz, *Int. J. Pharm.* 1987 35:7-12), fenofibrate (M. T. Sheu et al., *Int. J. Pharm.* 1994 103:137-146), prednisolone (R. Jachowicz, *Int. J. Pharm.* 1987 35:1-5) and glyburide (G. V. Betageri et al., *Int. J. Pharm.* 1995 126:155-160).

In WO 97/49384 published Dec. 31, 1997, J. McGinity and F. Zhang disclose pharmaceutical formulations comprising a hot-melt extrudable mixture of a therapeutic compound and a high molecular weight poly(ethylene oxide) (PEO) optionally containing polyethyleneglycol as a plasticizer. The PEO utilized in the invention had a molecular weight range from 1,000,000 to 10,000,000. This application was subsequently granted as U.S. Pat. No. 6,488,963.

In U.S. Publication No. 2004/0253314 published Dec. 16, 2004, H.-U. Petereit et al. disclosed melt extrusion formulations comprising an active pharmaceutical ingredient and a (meth)acrylate copolymer comprised of 40 to 75 weight % of radically copolymerized $C_{1-4}$ alkyl esters of acrylic acid or of methacrylic acid.

In U.S. Publication No. 2005/0048112 published Mar. 3, 2005, J. Breitenbach et al. disclose solid pharmaceutical dosage forms comprising a solid dispersion of at least one HIV protease inhibitor, at least one pharmaceutically acceptable water soluble polymer and at least one pharmaceutically acceptable surfactant wherein the water soluble polymer has a $T_g$ (glass transition temperature) of at least about 50° C.

In U.S. Publication No. 2005/0044529 published Apr. 21, 2005, J. Rosenberg et al. disclose solid pharmaceutical dosage forms comprising a solid dispersion of at least one HIV protease inhibitor, at least one pharmaceutically acceptable water soluble polymer and at least one pharmaceutically acceptable surfactant.

SUMMARY OF THE INVENTION

The present invention relates to a pharmaceutical composition comprising a solid suspension prepared by hot melt extrusion of isobutyric acid (2R,3S,4R,5R)-5-(4-amino-2-oxo-2H-pyrimidin-1-yl)-2-azido-3,4-bis-iso-butyryloxy-tetrahydro-furan-2-ylmethyl ester; hydrochloride salt (I; also referred to herein as 4'-azidocytidine-2',3',5'-tri-iso-butyrate hydrochloride) and a PEG/polypropylene glycol (PPG) block copolymer.

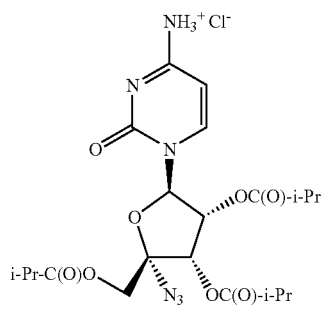

(I)

DETAILED DESCRIPTION OF THE INVENTION

The subject invention provides a pharmaceutical composition for orally administering I which comprises, based on the total weight of the composition, from about 250 mg to 500 mg of 4'-azidocytidine-2',3',5'-tri-iso-butyrate hydrochloride (I). The compound is described and claimed in U.S. Pat. No. 6,846,810 issued Jan. 2, 2005. A process to prepare the parent nucleoside is described by T. C. Connolly et al. in U.S. Publication 20050038240 published Feb. 17, 2005.

The triacylated nucleoside I has been found to decrease the viral load of patients infected with hepatitis C virus (HCV). Hepatitis C virus is the leading cause of chronic liver disease throughout the world (N. Boyer et al., *J. Hepatol.* 2000 32:98-112). Patients infected with HCV are at risk of developing cirrhosis of the liver and subsequent hepatocellular carcinoma and hence HCV is the major indication for liver transplantation. Although I is available in crystalline form, it has pH-dependent physicochemical properties. Moreover, the compound readily forms a gel when exposed to water and is difficult to process with aqueous solutions.

While some success formulating compounds with limited water solubility with solid dispersion formulations has been reported, each AI has unique properties and optimizing a formulation for a particular AI remains a challenging empirical endeavor. Effective dispersal on the active ingredient is required for optimal release. Hot melt-formulations require both the active ingredient and the carrier to exhibit adequate thermal stability. Thermal stability of the organic azide containing AI was a significant concern. Furthermore, chemotherapy of viral diseases frequently requires high doses to quickly lower the viral load and avoid conditions conducive to drug resistant mutations. The quantity of active ingredient in the dosage form required to produce high concentrations is large which further exacerbates solubility problems and limits the capacity for additional excipients which might otherwise be used.

One reason for the success of amorphous solutions and suspensions is the intimate contact of a hydrophilic carrier and the drug promotes wetting of the active ingredient and potentially increase the solubility of the AI in the diffusion layer surrounding the particle (Forster, supra). The incorporation of emulsifiers has been found to sometimes improve the wetting characteristics and solubility of compounds in solid solutions/suspensions. Surfactants such as sodium lauryl sulfate and Tween 80 enhanced release rates of naproxen from PEG4000, 6000 and 20,000 (C. Leuner and J. Dressman, supra).

It has now surprisingly been found that polyethylene glycol (PEG)/polypropylene glycol (PPG) block copolymers provide a desirable matrix for solid suspensions of I and improved bioavailability compared with other matrices. The compositions provided herein are amorphous suspensions wherein the block copolymer is amorphous phase in which crystalline I is suspended. The composition is prepared from a block copolymer with a melting point below that of I and maintaining the heating zones of the extruder at temperatures between the melting point of I and the copolymer.

The term "block copolymer" as used herein refers to a copolymer comprised of 2 or more blocks (or segments) of different homopolymers. The term homopolymer refers to a polymer comprised of a single monomer. Many variations of block copolymers are possible including simple diblock polymers with an A-B architecture and triblock polymers with A-B-A or A-B-C architectures. Poloxomers (or LUTROL®) are A-B-A block copolymers in which the A segment is a hydrophilic polyethylene glycol homopolymer and the B segment is hydrophobic polypropylene glycol homopolymer. Poloxomers are commercially available from BASF Corporation. Depending on the relative size of the blocks the copolymer can be a solid, liquid or paste. LUTROL® is a trademark of the BASF Corporation for poloxomers. The terms poloxomer and LUTROL are used interchangeably herein. Poloxomer 188 has an average molecular weight of about 8600 melting point of 52°-54° C. and HLB (hydrophilic-lipophilic balance) of 18-29 and the average particle size ranging from 1 micron to 500 microns. The polyoxyethylene units represent about 81% of the molecular weight. Poloxomer 188 is readily soluble in water. In the HCV prodrug formulation the block copolymer limits exposure to moisture which causes undesirable gelling of the AI. Other solid carriers which could be used to produce solid dispersions of I include Vitamin E TPGS (Eastman Kodak), Gelucire 44/14, Gelucire 50/13 (Gattefosse, N.J.), Solutol HS 15, poloxamer 407, LUTROL F77, Cremophor RH40 (BASF, NJ), sucrose dipalmitate and sucrose distearate (Croda, N.J.).

In one embodiment of the present invention there is provided a pharmaceutical composition comprising a solid suspension prepared by hot melt extrusion of iso-butyric acid (2R,3S,4R,5R)-5-(4-amino-2-oxo-2H-pyrimidin-1-yl)-2-azido-3,4-bis-iso-butyryloxy-tetrahydro-furan-2-ylmethyl ester hydrochloride salt (I) and a PEG/PPG block copolymer. In another embodiment of the present invention the solid suspension contains at least one carrier, diluent and/or excipient.

In yet another embodiment of the present invention there is provided a pharmaceutical composition which is a solid suspension of I and a poloxomer. In yet another embodiment of the present invention the pharmaceutical composition is a solid suspension of I and a poloxomer combined with at least one carrier, diluent and/or excipient. In still yet another embodiment of the present invention there is provided a solid suspension of I and a poloxomer is contained in a compressed table or a capsule which can also contain additional carriers, diluents and/or excipients.

In another embodiment of the present invention there is provided a pharmaceutical composition containing a solid suspension of I and poloxomer 188. In yet another embodiment of the present invention there is provided a pharmaceutical composition containing a solid suspension of I and poloxomer 188 where the solid suspension contains 20-40% by weight of poloxomer 188.

In another embodiment of the present invention there is provided a compressed tablet containing a solid suspension of I and poloxomer 188 containing microcrystalline cellulose, mannitol, crosprovidone, colloidal silicon dioxide, corn starch (or talc), magnesium stearate. In addition the compressed tablet can optionally contain sodium bicarbonate, arginine or maltodextrin and be optionally surrounded by a coating material.

In still yet another embodiment of the present invention there is provided a compressed tablet containing a solid suspension of I and poloxomer 188 wherein the solid suspension contains up to about 540 mg of I and about 175 to about 260 mg of poloxamer 188, about 125 mg to about 225 mg of microcrystalline cellulose (AVICEL® PH 101), about 70 to about 125 mg of mannitol (PARTECK™ 200), about 90 mg to about 150 mg of crospovidone (POLYPLASDONE® XL), about 10 to about 40 mg of colloidal silicon dioxide (AEROSIL® 380), about 10 to about 40 mg of corn starch (or talc), about 10 to about 25 mg of magnesium stearate. The tablet in this embodiment can optionally be coated with Opadry yellow 03K 12429.

In a further embodiment of the present invention there is provided a compressed tablet containing a solid suspension of I and poloxomer 188 wherein the solid suspension contains up to about 537 mg of I and about 230 mg of poloxamer 188, about 175 mg of microcrystalline cellulose, about 72 mg of mannitol, about 120 mg of crospovidone, about 24 mg of colloidal silicon dioxide, about 24 mg of corn starch (or talc) and about 18 mg of magnesium stearate and the compressed tablet is optionally coated with Opadry yellow 03K 12429.

In another embodiment of the present invention there is provided a compressed tablet containing a solid suspension of I and poloxomer 188 wherein the solid suspension contains up to about 537 mg of I and about 179 mg of poloxamer 188, about 175 mg of microcrystalline cellulose, about 123 mg of mannitol, about 120 mg of crospovidone, about 24 mg of colloidal silicon dioxide, about 24 mg of corn starch and about 18 mg of magnesium stearate and the compressed tablet is optionally coated with Opadry yellow 03K 12429.

In another embodiment there is provided a pharmaceutical composition containing a solid suspension of I, poloxomer and a plasticizer. In this embodiment the plasticizer increases flexibility, workability, or distensibility of the extrudate. In addition, a plasticizer may reduce the melt viscosity and lower the elastic modulus of the product. Plasticizers generally lower the glass transition temperature or softening point of the block copolymer in order to allow for lower processing temperature, less extruder torque and pressure during the extrusion process. Plasticizers also commonly lower the viscosity of the molten extrudate. Examples of plasticizers that can be used in accordance with the invention include: triacetin, propylene glycol, polyethylene glycol having a molecular weight of about 200 to about 1,000 (e.g., PEG 4600), dibutyl phthalate, dibutyl sebacate triethyl citrate, vegetable and mineral oils, fatty acids, fatty acid glycerides of $C_{6-18}$ fatty acids, e.g., Tween 80, and the like.

In another embodiment of the present invention there is provided a process for preparing a solid suspension of I and a PEG/PPG block copolymer comprising the steps of: (i) mixing the solids in a blender; (ii) introducing the resulting solids mixture into a heating zone of a hot melt extruder wherein the temperature of the heating zone is in a range above the melting point of said block copolymer and below the melting point of I; (iii) extruding the resulting melt; and, (iv) milling the solid suspension to a particle size of between about 20 and about 2000 microns. In another embodiment of present invention the particle size is milled to between about 100 to about 600 microns.

In another embodiment of the present invention there is provided a pharmaceutical composition comprised of a solid suspension of I and poloxomer 188 wherein the solid suspension is between about 55 and about 70% of I (w/w), about 5 to about 12% mannitol, about 13 to about 16% microcrystalline cellulose, about 8 to about 12% crospovidone, about 1 to about 3% colloidal silicon dioxide, about 1 to about 3% corn starch (or talc) and about 1 to about 2% magnesium stearate.

In one embodiment of the present invention the solid suspension along with carriers, diluents and excipients are incorporated into a compressed tablet. Excipients are incorporated along with the solid suspension to impart desirable properties. Useful excipients which are commonly included in compressed tablet formulations include binders, surfactants, diluents, compression aids, disintegrants, anti-adherents, stabilizers, anti-oxidants, colorants, wetting agents and lubricants. Carriers, diluents and expcipients which have proven useful are well known in the pharmaceutical arts and are described in *Remington: The Science and Practice of Pharmacy* 1995, edited by E. W. Martin, Mack Publishing Company, 19th edition, Easton, Pa. Many ingredients can used for several purposes even within the same formulation and the excipients and diluents included herein can be substituted for, or altered, without departing from the spirit of the invention.

The tablets containing the solid suspension are optionally coated. The membrane coating may further contain other coating excipients such as opacifiers, pigments, colorants and the like. The choice of such materials and the amounts to be utilized are considered to be within the art.

The term excipients as used herein refers to inert materials which impart satisfactory processing and compression characteristics into the formulation or impart desired physical characteristics to the finished table.

Diluents are inert ingredients added to adjust the bulk in order to produce a size practical for compression. Common diluents include dicalcium phosphate, calcium sulfate, lactose, cellulose, kaolin, mannitol, sodium chloride starch and powdered sugar. Diluents such as mannitol, lactose, sorbitol, sucrose and inositol in sufficient quantities aid disintegration of the tablet and are frequently used in chewable tablets. Microcrystalline cellulose (AVICEL®) has been used as an excipient in direct compression formula.

Binders are added to powders to impart cohesive qualities to the powder which allows the compressed tablet to retain its integrity. Materials commonly used as binders include starch, gelatin and sugars such as sucrose, glucose, dextrose, molasses and lactose. Natural and synthetic gums including acacia, sodium alginate, panwar gum, ghatti gum, carboxymethyl cellulose, methyl cellulose, polyvinylpyrrolidone, ethyl cellulose have also be used binders in some formulations.

Lubricants are employed to prevent adhesion of the tablet material to the surface of dyes and punches. Commonly used lubricants include talc, magnesium stearate, calcium stearate, stearic acid, hydrogenated vegetable oils and PEG. Water soluble lubricants include sodium benzoate, mixtures of sodium benzoate and sodium acetate, sodium chloride, leucine and Carbowax 4000.

Glidants are incorporated to improve the flow characteristics of the tablet powder. Colloidal silicon dioxide (AEROSIL®) is a common glidant. Talc may serve as a combined lubricant/glidant.

A disintegrant is a substance, or a mixture of substances added to facilitate breakup or disintegrate after administration. Dried and powdered corn starch or potato starch are popular disintegrants. They have a high affinity for water and swell when moistened leading to rupture of the tablet. A group of materials known as super-disintegrants include croscarmelose, a cross-linked cellulose, crosprovidone, a cross-linked polymer and sodium starch glycolate, a cross-linked starch. Crosprovidone (POLYPLASDONE®) is a synthetic, insoluble, but rapidly swellable cross-linked N-vinyl-pyrrolidone homopolymer.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof. The skilled pharmaceutical chemist will be aware of excipients, diluents and carriers which can be used interchangeably and these variations do not depart from the spirit of the invention.

EXAMPLE 1

The following composition represents a formulation based on a % by weight basis.

| Ingredient | Composition (w/w) |
| --- | --- |
| 4'-azidocytidine-2',3',5'-triisobutyrate HCl (I) | 44.73% |
| poloxamer 188 | 19.18% |
| microcrystalline cellulose | 14.59% |
| mannitol | 6.00% |
| crospovidone | 10.00% |
| colloidal silicon dioxide | 2.00% |
| corn starch | 2.00% |
| magnesium stearate | 1.50% |

One skilled in the art would recognize that as the quantity of I can be easily modified to produce tablets or capsules of different strengths by replacing some of the AI with additional diluent and that altering the quantity of I or the solid dispersion of I does not depart from the spirit of the invention.

The active ingredient I and poloxamer 188 and optionally a plasticizer are mixed in a blender. The blended solid was fed into a Leistritz twin screw extruder. The heating zones are adjusted to 45, 65, 65, 65, 65, 70, 75 and 80° C. Zone temperature variation was maintained at ±5° C. These conditions are sufficient to melt the poloxomer and excipients without melting I. The twin screws were operated at 100±30 revolutions per minute and the powder flow rate was between 5 and 20 g/min, preferably between 10 and 15 g/min. Under these conditions the polymer melts and forms a homogenous coating around the active ingredient. The extrudate is collected at room temperature (15 to 30° C.) in double lined polyethylene containers. The extruded material is passed through a Fitz Mill and the milled material was blended with AVICEL PH101, mannitol, POLYPLASDONE XL and corn starch (optionally with talc in place of corn starch). Finally magnesium stearate is added to the blended material. The milled particle size to a particle size is between 100 and 2000 microns. The resulting mixture is fed into a tabletting machine and compressed into kernels.

A coating suspension can be prepared by combining Opadry and purified water and mixing for 45 min until the Opadry is completely dispersed. The kernels are placed into a perforated coating pan and heated with inlet air of 45±5° C. with intermittent agitation until the exhaust air reaches 40±50° C. Thereafter the inlet temperature is increased to 60±5° C. and the kernels coated with a continuously stirred coating suspension using an air spray system calibrated to apply 25 mg of the film coat on a dry basis per tablet. The coated tablets are dried by jogging until the moisture content is less than 2%, after which the tablets are cooled to RT and stored in a tight double polyethylene-lined container.

EXAMPLE 2

The following compositions are prepared:

| | Composition | |
| --- | --- | --- |
| | Example 2a | Example 2b |
| Ingredient | | |
| 4'-azidocytidine-2',3',5'-triisobutyrate HCl | 536.80 mg | 536.80 mg |
| poloxamer 188 | 230.11 mg | 179.00 mg |
| AVICEL PH 101 | 175.09 mg | — |
| AVICEL PH 102 | — | 175.00 mg |
| PARTECK 200 | 72.00 mg | 123.20 mg |
| POLYPLASDONE XL | 120.00 mg | 120.00 mg |
| AEROSIL 80 | 24.00 mg | 24.00 mg |
| corn starch | 24.00 mg | 24.00 mg |
| magnesium stearate | 18.00 mg | 18.00 mg |
| Kernel Weight | 1200.0 mg | 1200.0 mg |
| Film Coat Composition | | |
| Opadry Yellow 03K 12429 | 35.00 mg | |
| Purified Water | 183.75 mg | |
| Film Coat Weight | 35.00 mg | |
| Total Film Coated Tablet Weight | 1235.0 mg | |

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A pharmaceutical composition comprising a solid suspension prepared by hot melt extrusion of isobutyric acid (2R,3S,4R,5R)-5-(4-amino-2-oxo-2H-pyrimidin-1-yl)-2-azido-3,4-bis-iso-butyryloxy-tetrahydro-furan-2-ylmethyl ester hydrochloride salt (I) and a polyethylene glycol (PEG)/polypropylene glycol (PPG) block copolymer.

2. A composition according to claim 1 further comprising at least one diluent, carrier and/or excipient.

3. A pharmaceutical composition according to claim 1 wherein said PEG/PPG block copolymer is a poloxomer.

4. A pharmaceutical composition according to claim 3 further comprising at least one diluent, carrier and/or excipient.

5. A pharmaceutical composition according to claim 3 comprising wherein said composition is contained in a capsule or a compressed tablet and said tablet or said capsule optionally contains one or more carrier, diluent and/or excipient.

6. A pharmaceutical composition according to claim 5 wherein said solid suspension comprises I and poloxomer 188.

7. A pharmaceutical composition according to claim 6 wherein said solid suspension is 20-40% (weight/weight) poloxomer 188.

8. A pharmaceutical composition according to claim 7 wherein the solid suspension is contained in a compressed tablet said tablet further optionally comprising one or more excipients selected from the group consisting of microcrystalline cellulose, mannitol, crosprovidone, colloidal silicon dioxide, corn starch (or talc), magnesium stearate sodium bicarbonate, arginine, maltodextrin and a coating material.

9. A pharmaceutical composition according to claim 8 wherein said compressed tablet comprises:

| Ingredient | Quantity |
| --- | --- |
| Compound I | about 540 mg |
| poloxamer 188 | 175 mg to 260 mg |
| microcrystalline cellulose | 125 mg to 225 mg |
| mannitol | 70 mg to 125 mg |
| crosprovidone | 90 mg to 150 mg |
| colloidal silicon dioxide | 10 mg to 40 mg |
| corn starch or talc | 10 mg to 40 mg |
| magnesium stearate | 10 mg to 25 mg | wherein said compressed tablet is optionally coated with Opadry yellow 03K 12429.

10. A pharmaceutical composition according to claim 9 comprising:

| Ingredient | Quantity |
| --- | --- |
| Compound I | 537 mg |
| poloxamer 188 | 230 mg |
| microcrystalline cellulose | 175 mg |
| mannitol | 72 mg |
| crosprovidone | 120 mg |
| colloidal silicon dioxide | 24 mg |
| corn starch or talc | 24 mg |
| magnesium stearate | 18 mg | wherein said compressed tablet is optionally coated with Opadry yellow 03K 12429.

11. A pharmaceutical composition according to claim 9 comprising:

| Ingredient | Quantity |
| --- | --- |
| Compound I | 537 mg |
| poloxamer 188 | 179 mg |
| microcrystalline cellulose | 175 mg |
| mannitol | 123. mg |
| crosprovidone | 120 mg |
| Colloidal Silicon Dioxide | 24 mg |
| corn starch or talc | 24 mg |
| Magnesium Stearate | 18 mg | wherein said compressed tablet is optionally coated with Opadry yellow 03K 12429.

12. A pharmaceutical composition comprising a solid suspension prepared by hot melt extrusion of isobutaric acid (2R,3S,4R,5R)-5-(4-amino-2-oxo-2H-pyrimidin-1-yl)-2-azido-3,4-bis-iso-butyryloxy-tetrahydro-furan-2-ylmethyl ester hydrochloride salt (I), a poloxomer 188 and a plasticizer.

13. A process for preparing a solid suspension of isobutaric acid (2R,3S,4R,5R)-5-(4-amino-2-oxo-2H-pyrimidin-1-yl)-2-azido-3,4-bis-iso-butyryloxy-tetrahydro-furan-2-ylmethyl ester hydrochloride salt (I) and a PEG/PPG block copolymer said process comprising the steps:
  (i) mixing the solids in a blender;
  (ii) introducing the resulting solids mixture into a heating zone of a hot melt extruder wherein the temperature of the heating zone is in a range above the melting point of said block copolymer and below the melting point of I;
  (iii) extruding the resulting melt; and,
  (iv) milling the solid suspension to a particle size of between about 20 and about 2000 microns.

14. The process according to claim 13 wherein the solid suspension is milled to between about 100 and about 600 microns.

* * * * *